United States Patent [19]

Maurer et al.

[11] 4,252,124
[45] Feb. 24, 1981

[54] SINGLE-ROD PH MEASURING CIRCUIT

[75] Inventors: Heinrich Maurer; Willy Möller, both of Zurich, Switzerland; Jean-Fred Quercy, Marly, France; Otto Stamm, St. Gallen, Switzerland

[73] Assignee: Hoffmann-La Roche Inc., Nutley, N.J.

[21] Appl. No.: 11,742

[22] Filed: Feb. 13, 1979

Related U.S. Application Data

[63] Continuation of Ser. No. 776,020, Mar. 9, 1977, abandoned.

[30] Foreign Application Priority Data

Mar. 12, 1976 [CH] Switzerland .................. 3092/76

[51] Int. Cl.³ .................. G01N 27/00; G01N 27/30
[52] U.S. Cl. .................. 128/635; 128/642; 204/195 G; 204/195 F
[58] Field of Search .............. 204/1 T, 195 G, 195 F, 204/195 M, 195 P; 128/2.06 E, 2.1 E, 635, 642; 324/30 R, 29, 438

[56] References Cited

U.S. PATENT DOCUMENTS

| | | | |
|---|---|---|---|
| 2,755,243 | 7/1956 | Beckman et al. | 204/195 G |
| 3,088,905 | 5/1963 | Glover | 204/195 P |
| 3,151,052 | 9/1964 | Arthur et al. | 204/195 F |
| 3,298,944 | 1/1967 | Luck | 204/195 F |
| 3,492,216 | 1/1970 | Riseman et al. | 204/195 M |
| 3,530,056 | 9/1970 | Haddad | 204/195 F |
| 3,598,712 | 8/1971 | Petersen | 204/195 G |
| 3,792,700 | 2/1974 | Sarnoff et al. | 128/2.06 E |
| 3,806,440 | 4/1974 | Gray et al. | 204/195 G |
| 3,973,555 | 8/1976 | Moller et al. | 204/195 G |
| 4,012,308 | 3/1977 | Jerrold-Jones | 204/195 G |

FOREIGN PATENT DOCUMENTS 941017  1/1974  Canada .................. 324/30 R

Primary Examiner—G. L. Kaplan
Attorney, Agent, or Firm—Jon S. Saxe; Bernard S. Leon; Mark L. Hopkins

[57] ABSTRACT

A single-rod pH measuring arrangement comprised of a pH-sensitive glass electrode and a reference electrode electrically communicating with the solution to be measured via a salt bridge. A plastic containing member partially surrounds the glass electrode in a manner providing an aperture through which the pH-sensitive part of the glass electrode projects. The edge of the plastic member lies adjacent to the surface of the glass electrode whereby the space between the two constitutes the salt bridge, with the latter being particularly insensitive to reference electrode problems such as solid protein layer deposition due to the blood coagulation system which leads to reference electrode potential instability.

14 Claims, 4 Drawing Figures

SINGLE-ROD PH MEASURING CIRCUIT

This is a continuation of application Ser. No. 776,020 filed Mar. 9, 1977 and now abandoned.

BACKGROUND OF THE INVENTION

The invention is concerned with a single-rod pH measuring circuit comprising a pH-sensitive glass electrode and a reference electrode which is in electrically conductive communication with the solution to be measured via a salt bridge.

For measuring of the hydrogen ion concentration in a test solution there is normally used a measuring electrode, principally a glass electrode, in conjunction with a reference electrode, whereby both electrodes are immersed in the solution to be measured.

Such an electrode combination is called a pH measuring circuit. Thereby, the reference electrode must deliver a constant reference potential independently of the composition of the test solution. On the other hand, there eventuates a potential at the glass electrode which is in exact function with the hydrogen ion concentration or the pH-value of the solution.

The variation in potential of a pH measuring circuit is measured with amplifiers of very high input impedance and is somewhat temperature dependent. The variation in potential is 59.2 mV per pH unit at 25° C.

The reference electrode normally consists of a vessel, principally of glass, filled with a suitable salt solution, preferably a concentrated aqueous solution of potassium chloride, sodium chloride or potassium nitrate. An electrode, usually calomel or silver-silver chloride, is immersed in this salt solution in order to derive the reference potential. The salt solution is in communication with the test solution via a suitable outflow aperture, hereinafter called the salt bridge. The outflow of the salt solution is normally attained by an elevated hydrostatic pressure as compared with the test solution. On the other hand, the too rapid outflow of salt solution must be prevented, wherefore the outflow aperture is usually formed from asbestos fibers, porous glass or ceramic rods, platinum strands, ground glass sleeves, one upon another.

The glass electrode consists of a glass tube which is closed at one end with a diaphragm consisting of electrically conductive special glass which is selectively sensitive to pH variations. The derivation of the diaphragm potential is effected via a buffer solution and a silver—silver chloride electrode.

On grounds of practical handling, the glass electrode and the reference electrode are often combined in a concentric structure. One then speaks of a single-rod pH measuring circuit or combination pH electrode.

The potentiometric pH measuring technique is one of the established analysis methods in applied and theoretical chemistry.

The pH influences the course of a large number of chemical reactions occurring in nature and industry, especially those of most biological-chemical processes.

In man the maintenance of the almost neutral reaction of the blood in the organism is a vital necessity, since a change in the acid-base equilibrium influences not only the ion antagonism and the respiratory function of the blood, but also completely determines in their properties the proteins in the blood, the cell membranes in the tissues and the enzymes.

In man, the pH range of the blood is fairly narrow-banded. In two test groups of twenty men and twenty women each, 95% of the pH values of capillary whole blood were only between 7.36 and 7.43.

If the pH value deviates from the mentioned range then there arise serious disturbances which can lead to brain damage and to death. Such phenomena occur relatively often in the foetus during birth and can cause permanent damage such as mental debility and paralysis.

As the extreme, pH values in the human organism are given pH 6.8 and 7.8.

The pH value is lowered (acidosis) in the case of oxygen deficiency, kidney failure and diabetic coma.

The pH value is increased (alkalosis) in the case of excessive breathing of oxygen in conjunction with anaesthesia or in the case of lasting acid loss, e.g. as a result of vomiting.

For years there has been used almost exclusively for the medical pH monitoring a discontinuous "in vitro method". It consists in blood-sampling by vein-puncture and subsequent "in vitro determination" of the pH value conventional apparatus.

In all cases, but especially in the case of those of obstetrics, there are present the following disadvantages:

1. Critical trends in the pH development are often only recognizable later.
2. An increased risk of infection results through many punctures.
3. The normal obstetric procedure is interfered with by the blood sampling.

In recent times there have been reported laboratory tests with special electrodes which are directly inserted into the blood vessels and which should permit the continuous pH measurement in living bodies ("in vivo").

However, continuous pH measurements in vivo in the case of foetuses have not hitherto been described and are regarded as technically impracticable, namely 1. because, during the birth, no sufficiently large vessel is present in the scalp which enables a safe introduction of such a special electrode, and
2. because, according to the present state of medical knowledge, a pH measurement outside the vessel gives no clinically usable result for the estimation of the foetal metabolic situation.

It has now surprisingly been found that the pH value in the interstitial space of the subcutis is the same as in the capillary blood and varies analogously as the changes in the pH value of the capillary blood. In the child's scalp, the interstitial space of the subcutis lies between the scalp and the periosteum. In the normal state, it embraces a gap of about 2 mm width which is filled with fine fibers, cell nuclei and tissue fluid.

The fact that, in the case of the foetus, pH measurements in the interstitial fluid of the subcutis give clinically equivalent results to intermittently undertaken pH analyses of capillary blood, is a completely unexpected finding having regard to previously accepted views in the relevant medical literature.

Most of the mentioned electrodes contain the measuring and reference electrodes built into an injection needle in order to protect these sensitive parts upon perforation of skin and tissue (see, e.g. U.S. Pat. Nos. 3,244,433; 3,244,436 and 3,415,731). Such an arrangement has a serious disadvantage: redox potentials, which occur at all metal surfaces, can influence the accuracy of the in vivo pH measurements. This source of error is not observable upon calibration of the electrodes, since the redox potentials remain constant in calibration buffer solutions. On the other hand, the redox potential of the blood can show fluctuations of 40 vM.

The redox potential of the blood may especially strongly influence pH measurements with an iridium needle (see e.g. U.S. Pat. No. 3,726,777).

However, the most important source of error in relation to the accuracy of the measurement is the unstable potential of the reference electrode relative to the test solution. In general, the coagulation system of the blood inactivates within a short time the salt bridge of the reference electrode by the deposition of solid protein layers. This is especially true for capillary tubes. There is thus the need for an insensitive salt bridge. For the stable formation of a reference potential it is necessary that a small amount of the reference solution flows out.

A further frequent source of error, especially with regard to the reliability of the measurement, consists in that the known constructions cannot ensure that the reference electrode is in electrically conductive contact with the solution to be measured via the salt bridge.

A dilution or contamination of the mentioned saturated reference solution can also occur by back diffusion. In the interest of a long service life it is necessary that the reference electrode can be opened, mechanically and chemically cleaned and further filled with fresh reference solution.

SUMMARY OF THE INVENTION

The invention has as a basis the object to provide a single-rod pH measuring circuit with the following properties: accuracy and reliability of measurement, simple manipulation and maintenance, economic industrial manufacture, miniaturization, long service life, water-tightness of the potential derivation component and mechanically robust construction.

In accordance with the invention this problem is solved by a single-rod pH measuring circuit of the initially-mentioned kind, which is characterized by a plastic container, which partly surrounds the glass electrode, with an aperture through which the pH-sensitive part of the glass electrode projects, and the edge of which lies adjacent to the surface of the glass electrode, whereby the space between the edge of the aperture and the glass surface constitutes the salt bridge.

BRIEF DESCRIPTION OF THE DRAWINGS

Embodiments of the invention and their individual advantages are now illustrated hereinafter on the basis of the accompanying drawings. In the drawings.

DESCRIPTION OF THE PREFERRED EMBODIMENT(s)

Figure 1:
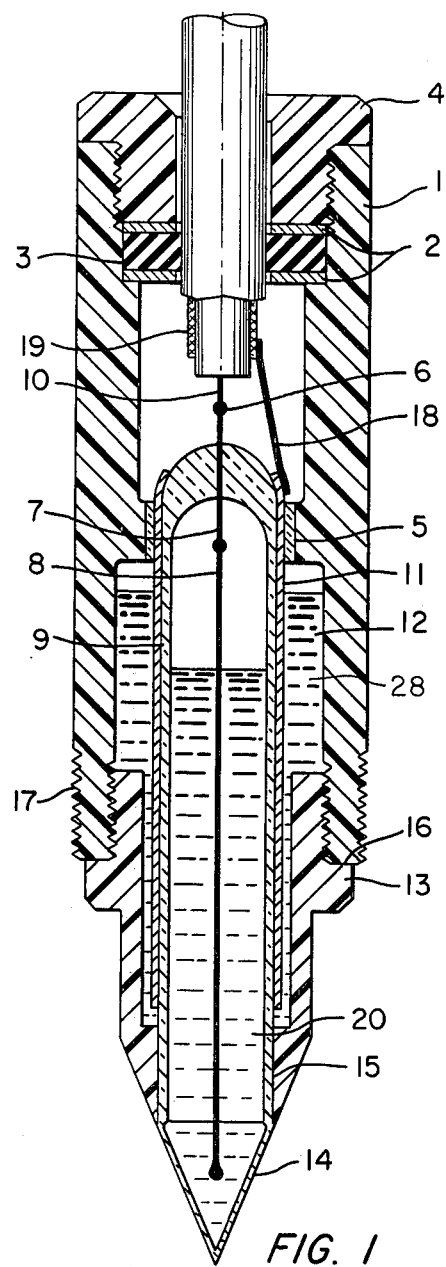
FIG. 1 shows a longitudinal section through the single-rod pH measuring circuit with coaxial derivation component.

A coaxial cable is inserted water-tight by means of a small but conventional stuffing box packing into a suitable housing 1 of plastic, such as polyacetal. This packing consists of pressure washers 2, rubber seal 3 and pressure screw 4. A conventionally manufactured pH glass electrode is embedded in this housing with a silicone adhesive 5. The derivation of the diaphragm potential is effected via chlorinated silver wire 8, a platinum bushing 7 through a glass electrode shank 9 with the aid of a soldered joint 6 on the internal conductor 10 of the coaxial cable. The derivation of the reference electrode is effected via a chlorinated silver layer 11 which, by means of a wire 18, is conductively connected with the sheath 19 of the coaxial cable. The silver layer is applied by cathode sputtering.

The chemical coating of a silver layer by reduction of an ammoniacal silver solution, or the evaporation of silver in a high vacuum forms a further possibility. The resulting thin silver layer makes possible a problem-free and tight passage of the reference potential, which would be more difficult with a wire since an additional bore would be required. The glass electrode contains a conventional electrolyte 20.

The silver layer is surrounded by a storage space 12 filled with reference solution 28.

A plastic component 13 screwable with the housing substantially determines the required electrode properties. In the following it is called the reference electrode shank. The reference electrode shank is bevelled at its front end so that it forms a continuous transition to the pH diaphgram 14, which is ground to a point, and therewith forms a cone suitable for the perforation of skin and tissue without requiring auxiliary devices such as an injection needle or scalpel. The contact surface formed by the close fit of the reference electrode shank 13 onto the glass shank 9 of the glass electrode represents the salt bridge 15, which has the following properties and advantages. In spite of a very large contact surface and a favorable electrical resistance, there is only established a very small, paractically negligible outflow of reference solution 28, and the tissue is accordingly irritated slightly. Through the anti-adhesive properties of reference electrode shank 13, no blocking of the salt bridge 15 by proteins occurs. A glass-on-glass joint of this size would only be manufacturable with substantially higher expense.

The salt bridge is situated in the immediate vicinity of the pH-sensitive diaphragm and is "heterogeneous", i.e. it results by the close contact of a predominantly hydrophobic plastic on a glass surface. The salt bridge is already cleaned simply by screwing on the reference electrode shank.

Simultaneously, the large release aperture facilitates inspection, cleaning and refilling of the reference electrode space.

By the mentioned layout of the aperture there is made possible an improved miniaturization as compared to e.g. a lateral filling aperture. By a well-dimensioned support 16 on the housing 1 the glass electrode is held stable by the reference electrode shank and protected from breaking. The reference electrode shank 13 can be unscrewed and screwed without tools. A securing device can be disposed on the thread 17 for suitable attachment of the electrode on the skin.

Figure 2:
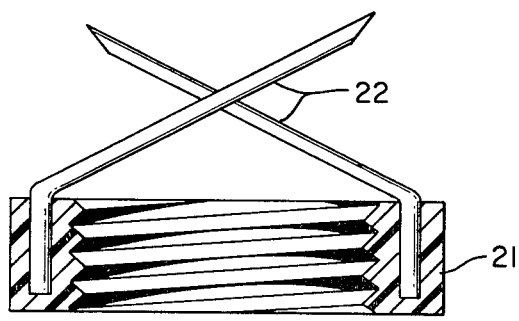
FIG. 2 shows a section through a securing device.

The securing device (FIG. 2) consists of a screw-threaded plastic ring 21, e.g. polyacetal, with two embedded spiral stainless-steel wires 22 ground to a point. The two wires can be secured in the skin by rotation with simultaneous forward pressure.

The part of the reference electrode shank which is inserted into the tissue has a diameter of about 2–3 mm and a length of 5–8 mm. The reference electrode is thus only surrounded by one layer of plastic.

The described construction of the single-rod pH measuring circuit has a slope of 56 mV to 59 mV per pH unit. In a wide-ranging clinical test it has been shown that the electrode does not deviate more than ±0.01 pH from the calibrated value even after several hours insertion in vivo.

Figure 3:
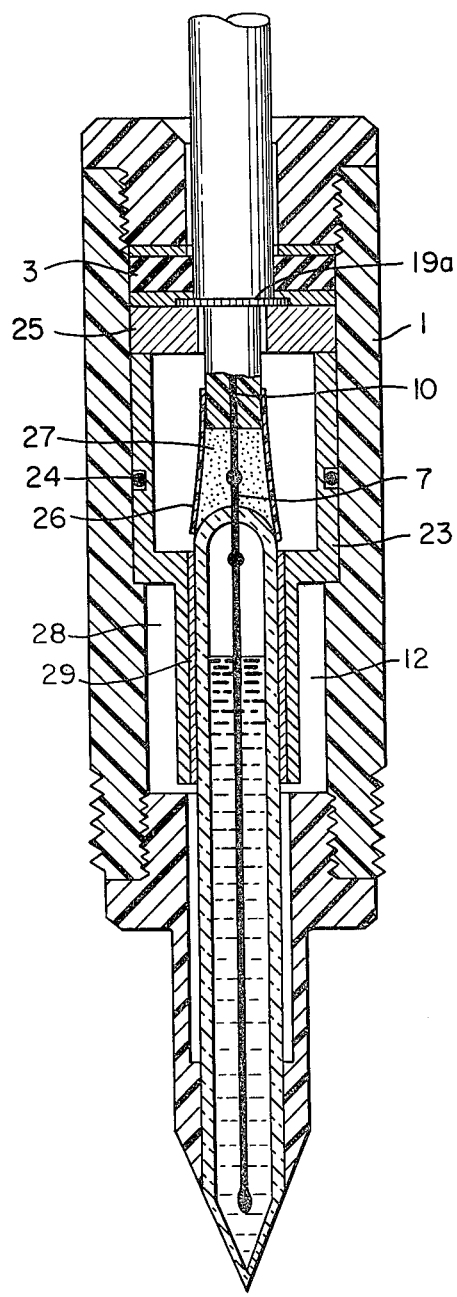
FIGS. 3 and 4 show alternative forms of pH measuring circuit.

In the case of the embodiment shown in FIG. 3, the reference potentials are derived by a concentric socket or sleeve 23 consisting of silver or silver-coated material. The socket 23 has at its lower part an internal diameter which corresponds to the external diameter of the glass electrode, and is stuck to the rear part of the glass electrode, i.e the part remote from the pH-sensitive tip via adhesive 29. By this adhesion there is formed an effective sealing of the storage space 12 for the reference solution 28. In the upper part the internal diameter of socket 23 is widened like a funnel in order to provide space for the electrical connection between the platinum wire bushing 7 and the inner conductor 10 of the coaxial cable and the isolation of the connection. The outer diameter of the socket 23 corresponds in its upper part with the internal diameter of the housing 1. For the sealing for the reference solution 28, an O-ring 24 is provided here into a corresponding groove in the outer surface of the socket. In the lower part, the external diameter of the socket is reduced so that the smallest possible space provided for the reference solution is required. On the other hand, the tapering lower part of the socket is relatively long, whereby a favorable supporting for the glass electrode is achieved, which is of advantage having regard to the relatively high mechanical stress of the glass electrode during puncturing.

The upper widened part of the socket 23 serves as the electrical screen of external interference for the connection between the coaxial cable and the internal derivation component of the measuring electrode. Simultaneously, the socket has the function to take on the mechanical forces which appear from the glass electrode and to transmit some via a metal plate 25 to the stuffing box packing 3 and thus to the housing 1. The plate 25 has the same outer diameter as the upper part of the socket 23 and a bore, the diameter of which corresponds with that of the internal insulating tube of the coaxial cable. The sheath 19a of the coaxial cable is bent outwards and bears on the upper surface of the metal plate 25. By the pressure of the stuffing-box packing there is guaranteed the electrical contact between the socket 23 and the metal plate 25 on the one hand as well as between the metal plate 25 and the sheath 19a on the other hand. By the metal plate 25 there is completed the screening of the contact between the derivation of the measuring electrode and the inner conductor of the coaxial cable.

The contact is additionally insulated by a shrink tube 26 and an epoxy resin filling 27.

This embodiment is suitable for extreme miniaturization and, on the other hand, offers a simple manufacturing possibility by its constructive design.

Figure 4:
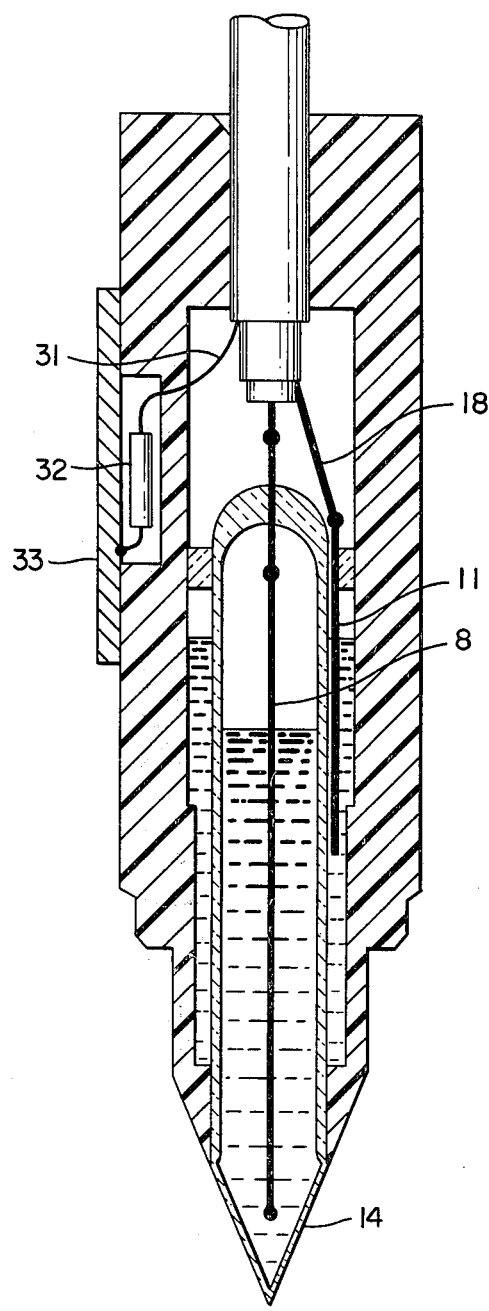

One embodiment, with which the reliability of the pH measurement can be substantially increased is shown in FIG. 4 in schematically simplified form. In addition to the two derivations of the measuring and the reference electrode, a third electric conductor 31 leads via a resistance 32 to a metal electrode 33 disposed on the outside of the housing. With this embodiment there can simultaneously be recorded with the measurement of the pH value a signal representing the heart action potential. In this case the reference electrode of the pH measuring circuit serves as the measuring electrode for this action potential and the metal electrode 33 serves as the associated reference electrode. This arrangement serves as the control for the right position of the salt bridge. The measured signals give information as to whether the salt bridge is in good contact with the medium to be measured. Where the electrical contact of the salt bridge with the medium is interrupted or disturbed, the measured signal changes or stops completely. In contrast to the reference electrode of the pH measuring circuit, the metal electrode 23 need not be in the immediate vicinity of the measuring electrode 14, since the contact of the reference electrode for the derivation of the heart action potential can be connected at an optional point to the patient. The resistance 32 serves for matching the impedance of the reference electrode to the relatively high impedance of the salt bridge.

The invention has been described on the basis of the most practically important and preferred embodiments. Of course, these can be varied in numerous ways without thereby departing from the scope of the invention.

What is claimed is:

1. Single-rod measuring circuit for pH measurement in living organisms, comprising a pH-sensitive first electrode, a reference electrode which is in electrically conductive connection with the solution to be measured via a salt bridge and which includes an electrolyte solution, and a container coaxial with said first electrode, said container having an aperture through which a pH-sensitive part of said first electrode projects, with the edge portion of the container which defines the aperture being adjacent to the surface of said first electrode, said edge of the container and said surface of the first electrode defining the salt bridge proximate the end portion of the projecting pH-sensitive part, said salt bridge being dimensioned to effect a restrained outflow of the electrolyte solution for continuous stable operation even over relatively long measuring periods.

2. Single-rod pH measuring circuit according to claim 1 wherein the container comprises two parts which are bound one to the other by a screw coupling.

3. Single-rod pH measuring circuit according to claim 2 wherein the juncture of the two parts of the container serves as a cleaning and filling port.

4. Single-rod pH measuring circuit according to claim 1 wherein the container has on its outer surface a thread for screwing on a securing device, said thread being located adjacent to the opening of the container through which the first electrode projects.

5. Single-rod pH measuring circuit according to claim 1 wherein the reference electrode comprises a metal layer deposited on the surface of the first electrode.

6. Single-rod pH measuring circuit according to claim 5 wherein the metal layer is comprised of a silver tube.

7. Single-rod pH measuring circuit according to claim 1 wherein the reference electrode simultaneously serves as an ECG electrode and wherein a reference electrode for ECG measurement is secured to the outside of the container.

8. A single-rod pH measuring circuit according to claim 1 wherein the reference electrode is comprised of a socket which is concentrically disposed around the part of the first electrode which is remote from the pH sensitive part of the first electrode and is mechanically connected to the first electrode.

9. Single-rod pH measuring circuit according to claim 8 wherein the socket partially surrounds the first electrode stem and its connection with a connecting cable as an electrical sheath.

10. Single-rod pH measuring circuit according to claim 9 wherein a metal plate is provided for the electrical connection between the socket and the connecting cable and for the mechanical reinforcement of the socket against the housing.

11. Single-rod pH measuring circuit according to claim 9 wherein the socket has a funnel-shaped form with a tubular prolongation in the direction of the pH-sensitive part of the first electrode.

12. A single-rod electrode arrangement for pH measurement in living organisms, comprising a first electrode having at least a projecting end portion which is pH-sensitive and adapted for insertion into a living organism, a reference electrode which is in electrically conductive connection with the solution to be measured within the organism via a salt bridge and including an electrolyte solution contained within the electrode arrangement, and a casing partially encompassing the first electrode and having an aperture through which the pH-sensitive portion of the first electrode projects, the portion of the casing which defines the aperture being configured to be adjacent to the surface of the first electrode to define an opening therebetween, which opening constitutes the salt bridge proximate the end of the projecting pH-sensitive portion of the first electrode by which the electrolyte solution flows into the organism to contact the solution to be measured, said opening being dimensioned to provide a substantially continuous restrained flow of the electrolyte into the organism for effecting stable operation over even relatively long measuring periods.

13. An electrode arrangement according to claim 12 wherein one of the adjacent portions of the casing and the first electrode which define the salt bridge has a hydrophobic surface property and the other a hydrophylic surface property.

14. A single-rod electrode arrangement for continuous stable pH measurement in living organisms over extended measuring periods, comprising a first electrode having at least a projecting end portion which is pH-sensitive and adapted for insertion into a living organism, a reference electrode which is in electrically conductive connection with the solution to be measured within the organism via a salt bridge and including an electrolyte solution contained within the electrode arrangement, and a casing partially encompassing the first electrode and having an aperture through which the pH-sensitive portion of the first electrode projects, the portion of the casing which defines the aperture being configured to be adjacent the surface of the first electrode to define an opening therebetween, which opening constitutes the salt bridge proximate the end of the projecting pH-sensitive portion of the first electrode by which the electrolyte solution flows directly into the organism to contact the solution to be measured, said opening being dimensioned to provide a substantially continuous restrained flow of the electrolyte solution into the organism and an electrolyte solution/organism solution junction substantially greater in size than the physical area of said opening.

* * * * *